United States Patent [19]

Goodale

[11] Patent Number: 4,620,540
[45] Date of Patent: Nov. 4, 1986

[54] MOLD FOR RAPID STEREOTAXIC INJECTIONS INTO MOUSE STRIATUM

[75] Inventor: David B. Goodale, Philadelphia, Pa.
[73] Assignee: Micromedical Research and Development Company, Philadelphia, Pa.
[21] Appl. No.: 788,346
[22] Filed: Oct. 17, 1985
[51] Int. Cl.⁴ .............................................. A61B 17/00
[52] U.S. Cl. .................. 128/303 B; 128/133; 264/222
[58] Field of Search ................ 128/303 B, 346, 133, 128/134; 604/116, 117, 174

[56] References Cited

U.S. PATENT DOCUMENTS 2,534,471 12/1950 Norheim ........................ 128/134 V
4,058,112 11/1977 Johnson .............................. 128/133

FOREIGN PATENT DOCUMENTS 662076 5/1979 U.S.S.R. ........................ 128/303 B

Primary Examiner—Richard E. Gluck
Attorney, Agent, or Firm—Steele, Gould & Fried

[57] ABSTRACT

A mold for stereotaxic injections into mouse striatum is disclosed which includes upper and lower mold halves defining therebetween a shaped interior cavity closely conforming to shape of the mouse head. Indentations are provided in the shaped cavity of the lower mold half to receive and retain therein the mouse upper incisors to longitudinally establish and set the position of the mouse head in the mold. A plurality of dowel pins project upwardly from the lower mold half and insert respectively into vertically registered, parallel, pin receiving openings provided in the upper mold half. One or more needle guide cannulae are secured in the upper mold half in precise alignment with a preselected nucleus area to receive and guide therethrough a skull piercing needle and secondly the needle of a micro-liter syringe.

10 Claims, 14 Drawing Figures

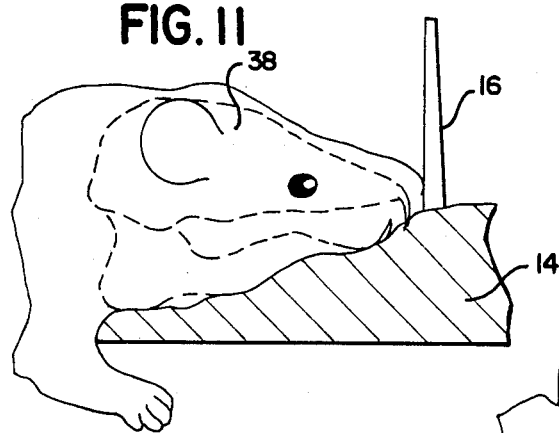
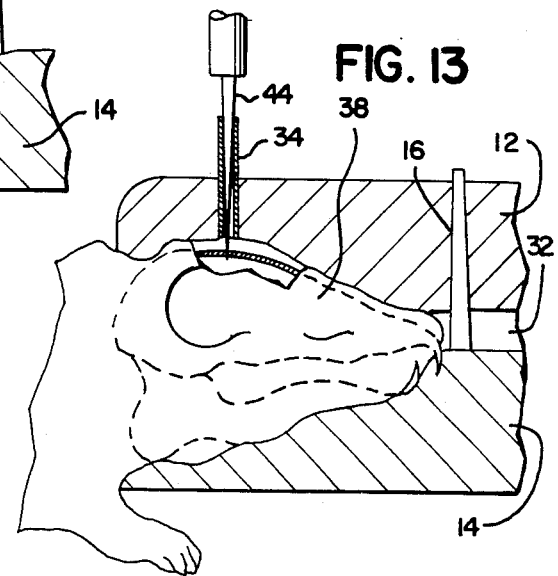
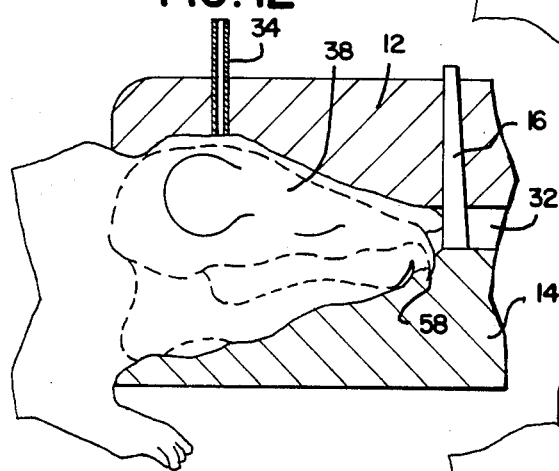
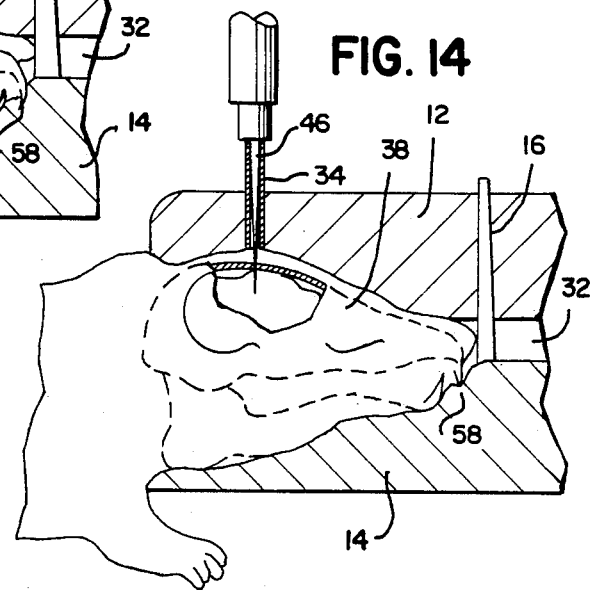

MOLD FOR RAPID STEREOTAXIC INJECTIONS INTO MOUSE STRIATUM

BACKGROUND OF THE INVENTION

1. Field of the Invention

The present invention relates generally to the field of small animal stereotaxic instruments, and more particularly, is directed to a mold useful to permit rapid, accurate stereotaxic injections into mouse striatum.

2. Description of the Prior Art

Instruments have been developed by prior workers in the art to facilitate stereotaxic injections into the striatum of small animals such as mice, rats, guinea pigs, monkeys, etc. Most such prior art instruments are equipped with locater bars which slide into the external portions of the ears of the animal in combination with a tooth bar and suitable screw drives to assure the accurate placement of the locater bars. One such device that is currently available is the Model 900 small animal stereotaxic instrument as manufactured and distributed by David Kopf Instruments, Tujunga, Ca.

The mouse has long been the experimental subject of choice for numerous basic biological disciplines such as pharmacology, immunology, hematology and oncology. More recently, there has been a growing number of neurological investigations using the mouse as an experimental animal inasmuch as mice have proven to be excellent subjects for investigations of such areas as learning, memory consolidation and neurobehavioral studies. The brain nuclei have been utilized to determine the effectiveness of a given treatment. For example, the apparatus and method of the present application could prove useful in investigating the effectiveness of treatments for Parkinson's disease.

In the past, because of their extremely small size and fragile structure, prior workers have experienced difficulty in firmly clamping the mouse head in a conventional stereotaxic machine using ear bars. Additionally, precision stereotaxic atlases of the mouse brain were not available to provide the required accurate locating of brain structures. However, more recently, publications such as a stereotaxic atlas for the forebrain of the deer mouse and another on the diencephalon of Mus Musculas by Montemurro & Dukelow together with a detailed account of cytoarchitectonic and myloarchitectonic features of the mouse brain by Kovac & Dank have become available. Additionally, a publication of the Public Health Service entitled "A Stereotaxic Atlas of the Albino Mouse Forebrain" by Slotnick & Leonard is also available.

However, when utilizing the prior art stereotaxic instruments in combination with the stereotaxic atlases for the accurate placement of cannulas, the procedure has proven to be as precise and time consuming as major surgery and usually requires an amount of time as much as from three quarters of an hour to an hour for each investigation. Additionally, the equipment utilized at the present time is quite expensive in construction and operation, all of which adds to the cost and expense involved in present studies. Accordingly, the need remains to provide an inexpensive, accurate and rapid apparatus and method for facilitating stereotaxic injections into mouse striatum.

As used herein, the term stereotaxic is derived from the Greek words "stereo" and "taxic" and should be interpreted as meaning solid holding to those knowledgeable in this field, this solid holding applies to the precise fixation of the heads of laboratory animals for accurate and repeatable placement of cannulas, probes or other surgical apparatus into the brain of the animal.

SUMMARY OF THE INVENTION

The present invention relates generally to the field of stereotaxic injections into mouse striatum, and more particularly, is directed to a method and apparatus for providing rapid and inexpensive stereotaxic injections into mouse striatum with acceptable accuracy.

The present invention includes a precision mold which has been especially designed to facilitate rapid and selective microinjections of known, suitable compounds into specific brain nuclei of mice. For example, the mold system of the present invention allows for the unilateral 6-hydroxydopamine-induced denervation of the striatal dopaminergic nerve terminals of approximately twenty mice per hour by one operator with complete accuracy. By utilizing the present precision mold, analysis can also be performed on such parameters as drug concentration, rate of injection and the type of anesthesia that is optimum for lesioning dopaminergic nerve terminals with 6-hydroxydopamine.

The precision mold comprises generally upper and lower mold halves or mold parts within which are formed corresponding impressions of the upper and lower portions of the head of a mouse. A plurality of dowel pins or positioning fingers are imbedded in one mold part and extended toward and enter into corresponding openings provided in the other mold part. A sufficient number of pins are utilized to assure precise alignment of the mold parts under all conditions of use and even after extended numbers of use cycles. One or more needle guide cannulas are positioned through the upper mold part in precise alignment with a preselected discrete nucleus area of the mouse brain. In this manner, by carefully and precisely positioning the head of the mouse within the mold, the cannulas may be employed to guide the usual needle of a syringe precisely into the desired nuclei for rapid and selective microinjections of preselected compounds.

Preferably, the lower mold half is provided with indentations suitable to receive the mouse's incisors therein to accurately and securely position the head of the animal with the mold. A breathing channel is provided through the upper mold half to facilitate free breathing of the mouse at all times while restrained within the mold.

In use, the mold parts are separated and the mouse is anesthetized in known manner. The head of the mouse is then introduced into the lower mold part and the incisors are carefully positioned within the indentations provided therefor. The upper mold part is then applied over the lower mold part by allowing the dowel pins or positioning pins to enter the corresponding openings. The mold parts are then brought completely together to snugly restrain the mouse's head therebetween in a predetermined, exact location. Preferably, the upper mold half is rearwardly provided with a depending posterior portion to rearwardly engage and firmly hold the mouse's head in place within the mold and to prevent any relative movement therebetween.

With the parts so positioned and with the mouse's head restrained in the preselected exact location within the mold, the needle guide cannula or cannulas will be situated and directed precisely above a preselected nucleus area or areas. A suitable needle of correct, preselected length is introduced downwardly through the needle guide cannula to pierce the mouse's skull bone (calvarium) and skin. Optionally, a limiting sheath on the needle can be employed to accurately limit the depth of thrust the needle so as to just pierce the thickness of the skin and the skull bone.

A conventional micro-liter syringe and injecting needle is then employed in usual manner to inject a preselected dosage directly into the nuclei. Preferably, a separate sheath is employed in conjunction with the micro-liter syringe injecting needle to precisely determine the depth of injection. It has been found that different nuclei will be present at different depths and accordingly, the proper depth for nucleus injection as determined from an atlas as previously discussed can be made. When investigation is to be made into more than one nucleus area of the mouse brain, then a separate mold with separately set cannulas should be provided for each such nucleus area.

By employing the novel mold of the present invention, it has been found that a single operator can now capable of performing selective microinjections into specific brain nuclei of approximately twenty mice per hour, a speed that was unheard of when utilizing the prior art apparatus and techniques.

It is therefore an object of the present invention to provide a novel mold for stereotaxic injections into mouse striatum that includes upper and lower mold halves, means for precisely aligning the mold halves, means for positioning and restraining a mouse head within the mold, means for aligning cannulas with preselected nucleus areas and means for the rapid injection of compounds into specific brain nuclei.

It is another object of the present invention to provide a novel mold for stereotaxic injections into mouse striatum which includes generally an upper mold half having formed therein an area conforming to the upper portion of the mouse head, a breathing channel communicating with the area, a posterior portion shaped to firmly hold the mouse head and precisionly positioned cannulas to register over preselected nuclei, a lower mold part having an area conforming to the lower half of a mouse head and means to repeatedly, accurately, and rapidly place a mouse head within the mold and dowel pin means to precisely and accurately align the mold parts.

It is another object of the present invention to provide an improved mold for stereotaxic injections into mouse striatum of the type set forth including the method of making the mold and the method of using the mold.

It is another object of the present invention to provide a novel mold for stereotaxic injections into mouse striatum that is simple in design, inexpensive in manufacture and both rapid and accurate when in use.

Other objects and a fuller understanding of the invention will be had by referring to the following description and claims of a preferred embodiment thereof, taken in conjunction with the accompanying drawings, wherein like reference characters refer to similar parts throughout the several views and in which:

BRIEF DESCRIPTION OF THE DRAWINGS

FIGS. 11-14 show successive steps employed in using the mold of the present invention.

DESCRIPTION OF THE PREFERRED EMBODIMENT OF THE INVENTION

Figure 1:
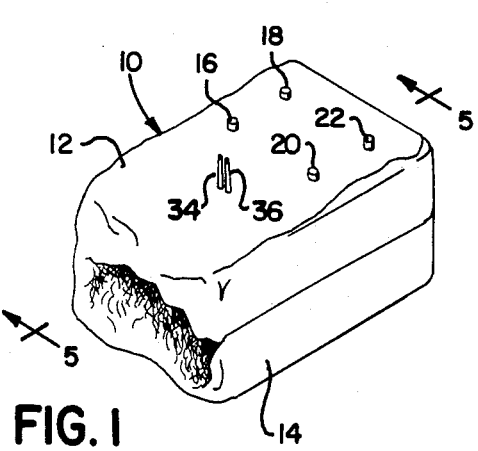
FIG. 1 is a rear perspective view showing the mold of the present invention.

Although specific terms are used in the following description for the sake of clarity, these terms are intended to refer only to the particular structure of the invention selected for illustration in the drawings, and are not intended to define or limit the scope of the invention.

Referring now to the drawings, there is illustrated in FIGS. 1-5 a mold of hard formable material, such as suitable plastic, clay or preferably dental stone. The mold is formed with cooperating upper and lower mold halves or parts 12, 14, which parts are maintained in precise alignment by a plurality of parallel guidance pins or dowels 16, 18, 20, 22 held in one mold part 14 and a plurality of vertically registered pin receiving openings 24, 26, 28, 30 provided in the cooperating mold half 12. The mold parts 12, 14 are formed about the head 38 of a mouse to provide cooperating, shaped lower and upper cavities 48, 50 of precisely the shape of the mouse head 38 as hereinafter more fully set forth. In the preferred embodiment, the upper mold part 12 is provided with a longitudinally extending breathing channel 32 which communicates the upper shaped cavity 50 with the surrounding ambient air. Preferably, the upper mold part 12 is rearwardly finished to define a depending posterior portion 56 (FIG. 10) of shape and size to bear against the rear of the mouse head 38 to firmly hold the head in place within the mold 10.

Figure 2:
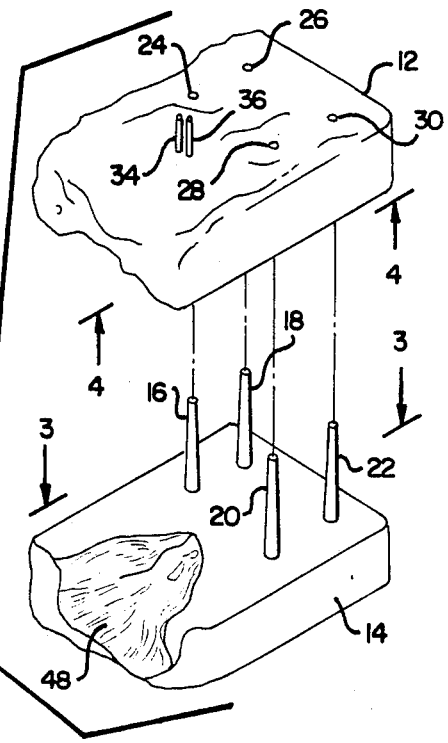
FIG. 2 is an exploded, perspective view of the mold of FIG. 1.
Figure 3:
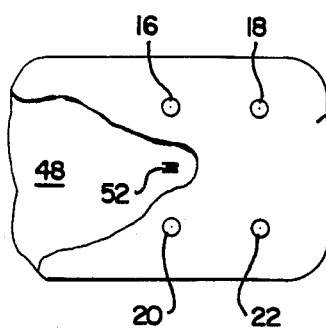
FIG. 3 is a plan view of the bottom mold half looking from line 3—3 on FIG. 2 in the direction of the arrows.
Figure 4:
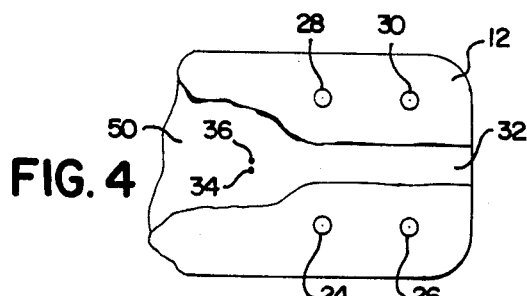
FIG. 4 is a bottom plan view of the upper mold half looking from line 4—4 on FIG. 2 in the direction of the arrows.
Figure 5:
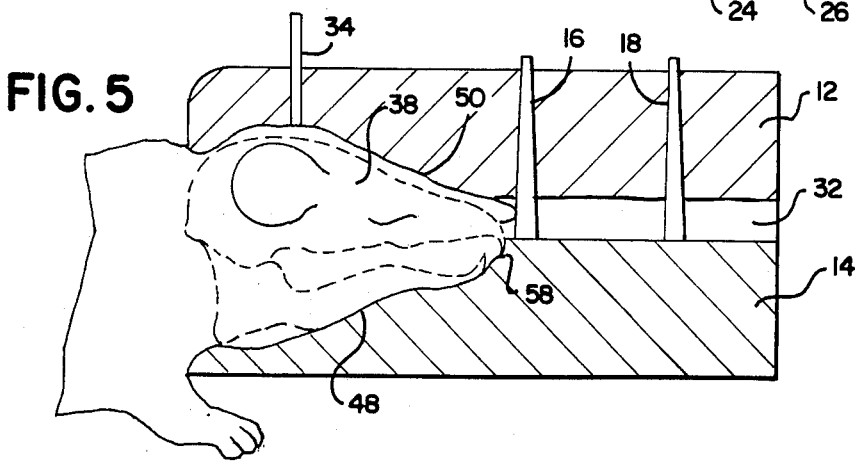
FIG. 5 is an enlarged, cross sectional view taken along line 5—5 on FIG. 1, and showing the head of a mouse restrained within the mold.
Figure 6:
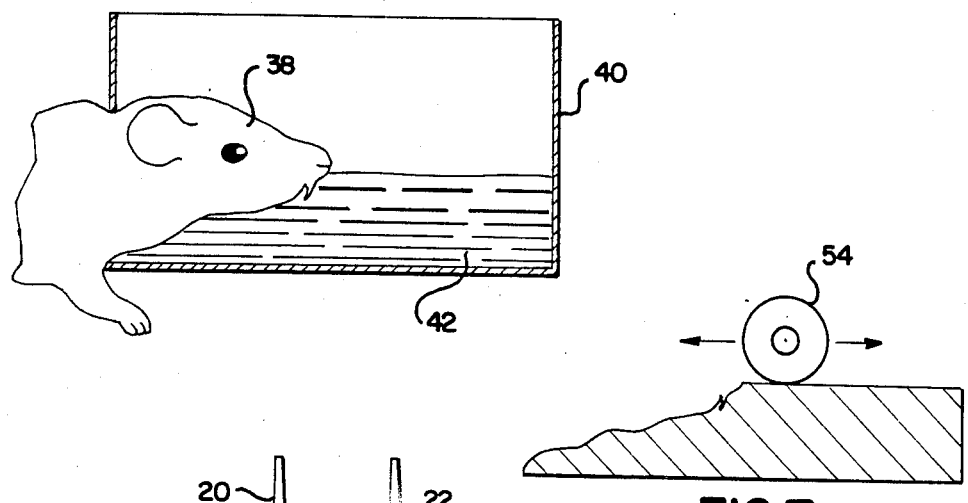
FIGS. 6-10 show successive steps utilized in forming the mold of the present invention.
Figure 7:
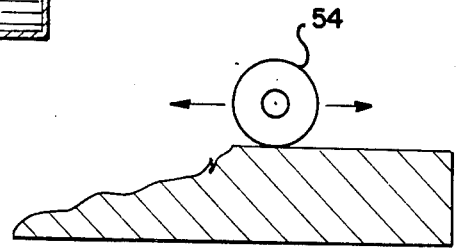
Figure 8:
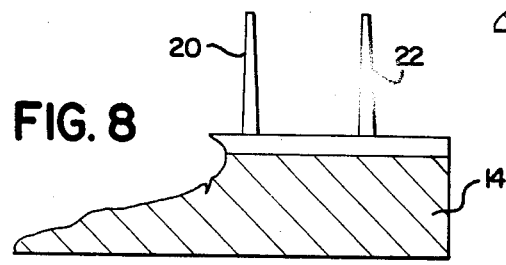

Inasmuch as the brain is a bilaterally symmetrical structure, it is preferable to employ two hollow needle guides of cannulas 34, 36 to precisely overlie corresponding nuclei (not shown) in the mouse's brain selected for investigation. The needle guide cannulas 34, 36 extend exteriorly of the upper mold part 12 to provide a depth limiting stop for the piercing needle or the syringe needle as more fully hereinafter discussed. The cannulas are positioned in the upper mold part 12 to terminate downwardly at the shaped surface which defines the upper shaped cavity 50. As best seen in FIGS. 2 and 3, the lower mold shaped cavity 48 is provided with special indentations of size, shape and position to receive and retain therein the incisors 58 of the mouse. In order to inject different specific nuclei, separate molds should be formed to position the cannulas 34, 36 to precisely register over each preselected nucleus area.

In use, the mouse head 38 is accurately restrained within the mold 10 by seating the upper incisor teeth 58 of the mouse 38 within the shaped tooth indentations 52. Then the upper mold part 12 is applied downwardly along the plurality of dowel or guidance pins 16, 18, 20, 22 until the upper shaped cavity 50 is brought snugly and precisely over the top of the mouse head 38. Once the mold has been assembled with the mouse head therewithin, movement of the head 38 relative to the mold 10 will be prevented in the anterior and posterior directions by the interaction of the incisors 58 and the shaped tooth indentations 12 in combination with the detent action of the depending upper mold part posterior portion 56. Relative movement in either lateral direction will be prevented by the cooperating lateral sides of the upper and lower shaped cavities 48, 50. Once the mouse head has been securely positioned in the manner illustrated in FIG. 5, microinjections of preselected compounds can then be made directly into the nuclei through the needle guide cannulas 34, 36.

In order to form the mold 10 in accordance with the teachings of the present invention, and referring particularly to FIGS. 6 through 10, a plastic or other suitable material forming mold 40 is employed in conventional manner to receive a quantity of dental stone or clay 42 in liquid or plastic consistency. A mouse head 38 is then applied directly to the wet dental stone or clay to form an exact shaped lower cavity 58 which conforms precisely to the configuration of the lower portion of the mouse head 38. The incisor teeth from a fixed portion of the mouse skull and are utilized to form the incisor indentations 52. By placing the incisors 58 of subsequent mice into the indentations 52, the skull will be fixed and accurately located in the anterior and posterior directions. Upon hardening of the clay or dental stone 42, the lower mold half 14 can be removed from the forming mold 40 and the top surface thereof is smoothed and otherwise worked as necessary, for example, by employing a conventional grinding wheel 54. Following grinding, the lower mold half can be drilled to receive the plurality of dowel pins 16, 18, 20, 22 in known manner in precise parallel arrangement. Preferable the dowel pins are set in their desired positions by employing glue. See FIG. 8.

Figure 9:
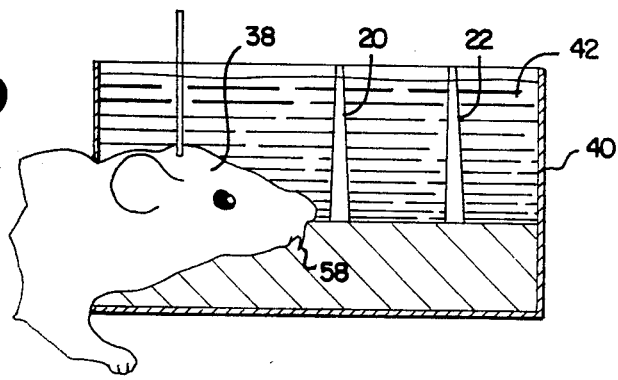

With the guidance or dowel pins properly positioned, the lower mold half 14 can then be reinserted within the forming mold 40 in the manner illustrated in FIG. 9 with the mouse head 38 properly positioned. Additional dental stone 42 can then be applied over the lower mold half 14 and over the head 38 of the mouse to form the upper mold part 12 having the upper shaped cavity 50 formed therein. It will be noted in FIG. 9 that stainless steel needle guide cannulas have been previously positioned within the mouse head 38 in alignment with the preselected nuclei areas prior to forming the upper mold half 12. The cannulas 34, 36 are precisely seated within the mouse's head 38 by using the previously mentioned prior art stereotaxic injection machines. While such prior art machines have been previously criticized because of the extended required set up and operating time necessary to accurately position the cannulas, it will be appreciated that such prior art machines need be utilized only a single time for use in the formation of the mold 10 of the present invention. After the mold has been fabricated in the manner herein set forth, the mold can then be rapidly used in a repetitious manner without need to again refer to the slower and more expensive prior art stereotaxic injection machines.

Figure 10:
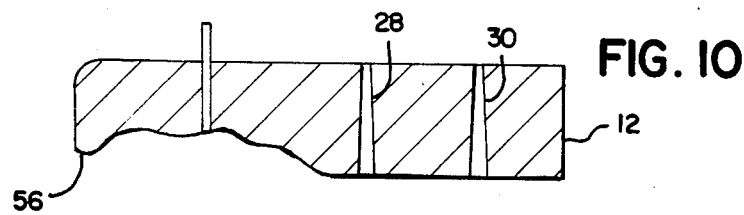

Upon hardening of the dental stone 42 in the upper mold half 12, as illustrated in FIG. 10, it will be noted that the upper mold half 12 can be removed from the forming mold 40 and the plurality of pin receiving openings 24, 26, 28, 30 will be automatically formed therein in correct alignment with the pins 16, 18, 20, 22. Additionally, the needle guide cannulas 34, 36 will be secured within the upper mold part 12 in the precise desired location as accurately determined by the prior art stereotaxic injection machine (not illustrated). Preferably, the lower or bottom end of the cannulas can be raised or glued or otherwise worked to terminate coincident with the peripheral surface of the upper shaped cavity 50.

After the mold 10 has been formed in the manner hereinbefore set forth, and referring to FIGS. 11, 12, 13 and 14, the use of the device can now be described. As illustrated in FIG. 11, the mold halves 12, 14 are separated and a previously anesthetized mouse is introduced to the lower mold half 14 within the lower shaped cavity 48 by carefully positioning the incisors 58 within the shaped tooth indentations 52 provided therefor. With the mouse's head 38 properly positioned, and as illustrated in FIG. 12, the upper mold part 12 is then applied over the lower mold part by inserting the plurality of guidance pins 16, 18, 20, 22 within the corresponding upper half openings 24, 26, 28, 30 and then pushing the parts together. When the upper mold part 12 is fully seated upon the lower mold part 14, the upper shaped cavity 50 and the lower shaped cavity 48 will engage the mouse head 38 in overall contact and will snugly hold the head with the preselected nucleus area precisely aligned beneath the needle guide cannulas 34, 36.

As illustrated in FIG. 13, with the mouse head 38 properly restrained within the continuous chamber defined by lower and upper shaped cavities 48, 50, a suitable needle 44 of proper length to just pierce the skin and skull in precise registry over the preselected nuclei is inserted downwardly through each of the needle guide cannulas 34, 36. Preferably, a depth positioning sleeve (not illustrated) can be applied over the cannulas 34, 36 to precisely limit the depth of penetration of the needle 44 to the exact, preselected depth, as determined from a suitable atlas.

After the skin and skull of the mouse head 38 have been pierced by the needle 44, the needle is withdrawn from the cannulas 34, 36 and a conventional micro-liter syringe 46 is employed to inject a preselected quantity of medication directly into the nucleus area undergoing study. In order to precisely control the depth of penetration of the syringe needle, a depth positioning sleeve (not illustrated) can be employed in conjunction with the cannulas 34, 36.

It is thus seen that precise and easily repeated injections may be made into the nuclei of a plurality of mice in a minimum amount of time by employing the mold 10 and the method of the present invention. After the mold has been properly formed, the need to take precise and individual measurements for the skull of each individual mouse can then be completely eliminated and the mold functions to assure complete uniformity and accuracy of injections in a rapid and reliable manner.

Although the present invention has been described with reference to the particular embodiments herein set forth, it is understood that the present disclosure has been made only by way of example and that numerous changes in the details of construction may be resorted to without departing from the spirit and scope of the invention. Thus, the scope of the invention should not be limited by the foregoing specification, but rather, only by the scope of the claims appended hereto.

What is claimed is:

1. A mold for stereotaxic injections into mouse striatum comprising a lower mold half comprising a lower block having a shaped lower cavity conforming to the shape of the lower half of a mouse head, the shaped lower cavity being provided with indentations of size, shape and location to receive therein the mouse upper incisors;

a plurality of dowel pins upwardly projecting from the lower block; and an upper mold half in registry about the lower mold half, the upper mold half comprising an upper block having a shaped upper cavity conforming to the shape of the upper half of the mouse head, the upper block being provided with a plurality of openings each located to receive therein respectively one of the said dowel pins; and at least one needle guide cannula secured in the upper block and extending into the shaped upper cavity;

wherein the needle guide cannula can be secured in the upper mold half in precise registry over a preselected nucleus area in the mouse head.

2. The mold of claim 1 wherein the upper mold half is rearwardly formed with a posterior portion, the posterior portion depending below the upper shaped cavity and being positioned to bear snugly against a posterior portion of the mouse head.

3. The mold of claim 1 wherein the upper and lower mold halves are formed with mating surfaces positioned laterally on each side of the respective shaped cavities.

4. The mold of claim 1 wherein the dowel pins extend through a mating surface of the lower mold half.

5. The mold of claim 4 wherein the plurality of openings terminate at a mating surface of the upper mold half.

6. The mold of claim 1 and a breathing channel formed in the upper mold half, the breathing channel communicating with the said shaped upper cavity.

7. The mold of claim 3 and a breathing channel formed in the upper mold half, the breathing channel communicating with the said shaped upper cavity.

8. The mold of claim 7 wherein a portion of the mating surface of the lower mold half forms a part of the periphery of the breathing channel.

9. The method of using a mold for stereotaxic injections into mouse striatum wherein the mold comprises a shaped cavity, an upper mold half containing an upper portion of the shaped cavity and a cannula secured in the upper mold half in communication with the shaped cavity and a lower mold half containing a lower portion of the shaped cavity and mouse incisor indentations in the said lower portion comprising placing a mouse head into the lower mold half and positioning the mouse upper incisors in the incisor indentations;

applying the upper mold half over the lower mold half and securing the mouse head therebetween;

aligning a preselected nucleus area of the mouse head directly beneath the cannula;

downwardly inserting a needle through the cannula sufficiently to pierce the skin and skull of the mouse head in direct alignment with the said nucleus area;

withdrawing the needle and applying a preselected quantity of medication directly into the nucleus area with a micro-liter syringe; and withdrawing the syringe, separating the mold halves and removing the mouse from the mold.

10. The method of use of claim 9 and providing a breathing channel in communication with the shaped cavity and permitting the mouse to breath through the breathing channel while restrained within the mold.

* * * * *